United States Patent [19]

Hadd

[11] Patent Number: 4,466,952
[45] Date of Patent: Aug. 21, 1984

[54] COMPOSITIONS AND PROCESS FOR THE TREATMENT OF CANCER

[75] Inventor: Harry E. Hadd, Valparaiso, Ind.

[73] Assignee: Indiana University Foundation, Bloomington, Ind.

[21] Appl. No.: 457,384

[22] Filed: Jan. 12, 1983

[51] Int. Cl.³ .................... A61K 43/00; A61K 49/00; C01J 41/00

[52] U.S. Cl. .................... 424/1.1; 260/397.5; 424/9; 424/148; 568/1

[58] Field of Search .................... 260/397.4, 397.5; 424/1.1, 9, 148; 568/1

[56] References Cited

U.S. PATENT DOCUMENTS 4,260,736 4/1981 Asano et al. .................... 260/397.5

OTHER PUBLICATIONS

Hawthorne et al., J. Med. Chem., vol. 15, (1972), pp. 449–452.

Raynaud et al., Cancer Research, vol. 38, (1978), pp. 3044–3050.

Kahl and Wolff, Aug. 29, 1980, "The Synthesis and Properties of Some Boron-Containing Steroids for Use in Boron Neutron Cancer Therapy", presented at Second Chemical Congress of the North American Continent, Las Vegas, Nevada.

Sweet and Samant, "Boron Derivatives of Estradiol and Testosterone for $^{10}$B–Neutron Capture Therapy of Cancers of the Female and Male Reproductive Systems", Jun. 1982.

Sweet, Boron Estrogens: "Synthesis, Biochemical and Biological Testing of Estrone and Estradiol-17β 3-carboranylmethyl Ethers", (Steroids 37, 223-238, (1981).

Hatanaka, "A Revised Boron–Neutron Capture Therapy for Malignant Brain Tumors", J. Neurol., 209, 81-94, (1975).

Brownell, Zamenhof, Murray, and Wellum, Chapt. 18, "Boron Neutron Capture Therapy", in Nuclear Medicine, (1977, Spencer, ed.).

Primary Examiner—Christine M. Nucker
Attorney, Agent, or Firm—Kirkland & Ellis

[57] ABSTRACT

Novel estratriene and estratetraene compositions bearing a dicarbadodecaboranyl substituent at the 17-position have been prepared which possess high uterotropic and estrophilic activity useful in boron neutron capture destruction of cancerous cells.

8 Claims, No Drawings

COMPOSITIONS AND PROCESS FOR THE TREATMENT OF CANCER

BACKGROUND OF THE INVENTION

1. Field of the Invention

The present invention relates to the preparation and use of novel estratriene and estratetraene compositions bearing a dicarbadodecaboranyl substituent at the 17-position useful in the destruction of cancerous cells containing estrogen receptors by boron-neutron capture therapy.

2. Description of the Prior Art

It is known that the non-radioactive boron isotope ($^{10}_5B$), on capture of a low-energy thermal neutron, emits a 2.33 MeV short-range alpha particle that is fatal to cells in a reaction that may be depicted as follows:

$$^{10}_5B + ^1_0n \rightarrow ^7_3Li + ^4_2He + 2.33 \text{ MeV}$$

Therefore, if $^{10}_5B$ nuclei of sufficiently high concentration are imbedded in cancerous cells and irradiated with thermal neutrons, cancerous tissues may be selectively destroyed.

Prior art methods for boron neutron capture therapy in the treatment of tumors suffered from a number of deficiencies. Many boron compounds which were tested in thermal neutron therapy failed to be stable in vivo, were toxic, or were non-tumor specific.

It has been suggested that estrogen compounds containing $^{10}_5B$ nuclei would be useful in the treatment of cancers which are localized in areas bearing estrogen receptors, such as cancer of the breast, uterus and endometrium. For example, Sweet (Steroids 37, 223–238 (1981)) described the preparation of "estradiol-17β 3-carboranylmethyl ether". However, Sweet's compound had very low uterotopic and estrophilic activity, and therefore, it is not useful in the destruction of cancerous tissue containing estrogen receptors.

It is therefore an object of this invention to produce estratriene and estratetraene compositions bearing a dicarbadodecaboranyl substituent at the 17-position useful for boron neutron capture therapy of cancerous tissues. It is a further object of this invention to produce estratriene and estratetrane compositions bearing a dicarbadodecaboranyl substituent at the 17-position which are stable in vivo, and which possess high uterotropic and estrophilic activity.

SUMMARY OF THE INVENTION

The foregoing and other objects, advantages and features of this invention may be achieved by the preparation and use of an estratriene composition bearing a dicarbadodecaboranyl substituent at the 17-position of the general formula:

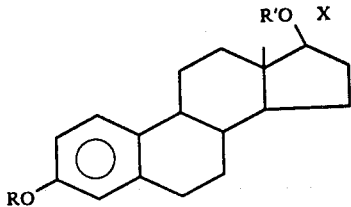

or an estratetraene of the general formula:

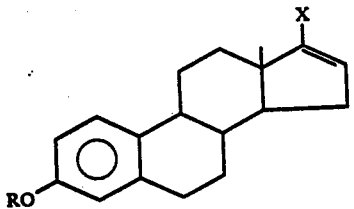

wherein R, and R' are selected from the group comprising hydrogen (—H), acetyl ($CH_3CO$—), and methyl (—$CH_3$), and wherein X denotes the dicarbadodecaboranyl substituent [$C_2B_{10}H_{11}$]:

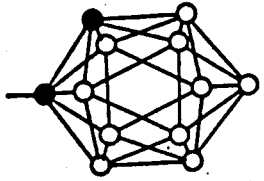

wherein ● denotes a carbon atom, and ○ denotes a boron atom. (For clarity, the hydrogen atoms are not shown.)

Estratriene and estratetraene compositions bearing a dicarbadodecaboranyl substituent at the 17-position are readily prepared by a condensation reaction of decaborane with precursor estratriene or estratetranene compositions that contain an ethinyl group at the 17-position. The progress of this condensation reaction can be conveniently monitored by thin-layer chromatography (TLC). The preparation of six novel estratriene and estratetraene derivatives containing a dicarbadodecaboranyl substituent at the 17-position is described in more detail below.

The estratriene or estratetraene compositions bearing a dicarbadodecarboranyl substituent at the 17-position, when administered, enter into the cell cytoplasm, bind to the cytosol estrogen receptor, and translate to the cell nuclei where they are bound to the DNA. Upon irradiation of a cell containing the complex formed by the binding of the dicarbadodecaboranyl estratriene or estratetraene and the cytosol estrogen receptor, the $^{10}_5B$ nuclei capture a thermal neutron which then decay to form high energy, short range alpha particles (i.e., less than about 10 microns). These alpha particles bring about cellular death within the cancerous tissue.

DETAILED DESCRIPTION OF THE INVENTION

The compositions of the present invention are generally designated as estratriene compositions bearing a dicarbadodecaboranyl substituent at the 17-position which contain different substituents at the 3, 17α, and 17β positions, as shown below.

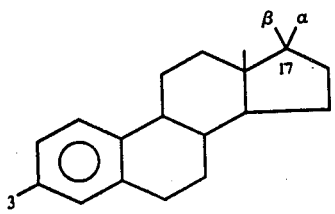

Alternatively, the compounds are estratetraenes as shown below.

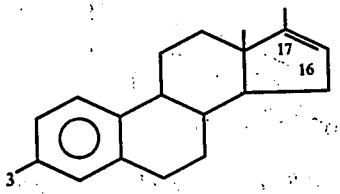

The estratriene or estratetrene compositions useful in the destruction of cancerous cells all bear a dicarbadodecarboranyl substituent at the 17-position:

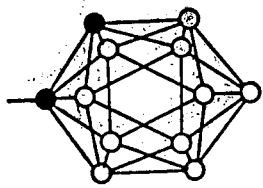

wherein ● = carbon atom, ○ = boron atom. The compounds of the present invention and their precursors are tabulated below in Tables I and II.

TABLE I

| | ESTRATRIENE COMPOSITIONS | | |
|---|---|---|---|
| Compound | 3 | 17α | 17β |
| I | —OAc | ethinyl | —OAc |
| II | —OAc | dicarbadodecaboranyl | —OAc |
| III | —OH | dicarbadodecaboranyl | —OAc |
| IV | —OH | | —OH |
| V | —OMe | ethinyl | —OAc |
| VI | —OMe | dicarbadodecaboranyl | —OAc |

TABLE II

| | ESTRATETRAENE COMPOSITIONS | |
|---|---|---|
| Compound | 3 | 17 |
| VII | —OMe | dicarbadodecaboranyl |
| VIII | —OAc | dicarbadodecaboranyl |

The estratriene compositions of the present invention are conveniently prepared from their corresponding acetylenic-estratriene precursors as follows. An estratriene containing an ethinyl substituent at the 17-position is reacted with decaborane in a dry-refluxing organic solvent until the condensation reaction is complete, as monitored by thin-layer chromatography. The reaction time generally takes from about 24 to about 72 hours when the reaction is carried out in refluxing benzene-acetonitrile. Of course, as one skilled in the art would expect, other refluxing solvents may be used which will affect the time necessary to complete the condensation. The products of the condensation may be conveniently separated by dry column chromatography, thin layer chromatography, high pressure liquid chromatography and other chromatographic methods, as well as combinations thereof.

When (17α)-19-norpregna-1,3,5(10)-trien-20-yne-3,17-diol diacetate(I) was condensed with decaborane in refluxing benzeneacetonitrile, 17-(1,2-dicarbadodecaboran(12)-1-yl)estra-1,3,5(10),16-tetraen-3-ol acetate (VIII) was formed, in addition to the expected product, (17β)-17-(1,2-dicarbadodecaboran(12)-1-yl)estra-1,3,5(10)-triene-3,17-diol diacetate(II).

The free diol, (17β)-17-(1,2-dicarbadodecaboran(12)-1-yl)estra-1,3,5(10)-triene-3,17-diol-3,17-diol(IV) may be prepared by hydrolysis, in base, of the diacetyloxy precursor (II) in methanol. As one skilled in the art would expect, the hydrolysis may be effected using different bases in different solvents.

When (17α)-3-methoxy-19-norpregna-1,3,5(10)-trien-20-yn-17-ol acetate(V) was condensed with decaborane in benzeneacetonitrile, 1-(3-methoxyestra-1,3,5(10),16-tetraen-17-yl)-1,2-dicarbadodecaborane(12)(VII) is formed by the loss of one mole of acetic acid per mole of (V), in addition to the expected product, (17β)-17-(1,2-dicarbadodecaboran(12)-1-yl)-3-methoxyestra-1,3,5(10)-trien-17-ol acetate(VI).

(17β)-17-(1,2-dicarbadodecaboran(12)-1-yl)estra-1,3,5(10)-triene-3,17-diol 17-acetate(III) is prepared by the mild base hydrolysis of 3, (17β)-17-(1,2-dicarbadodecaboran(12)-1-yl)estra-1,3,5(10)-triene-3,17-diol diacetate(II) (KHCO₃ in 92% methanol-8% water). Again, as one skilled in the art would expect, the hydrolysis may be effected by the use of bases other than KHCO₃, in solvents other than methanol/water.

Uterotopic assay indicates that (17β)-17-(1,2-dicarbadodecaboran(12)-1-yl)estra-1,3,5(10)-triene-3,17-diol 17-acetate(III) had at least 63% of the uterotopic response of estrone. Estrophilic activity of (III) is about two orders of magnitude greater than that reported for "estradiol-17β 3-carboranylmethyl ether".

The mechanism by which the estratriene or estratetraene compositions bearing a dicarbadodecaboranyl substituent at the 17-position enter a cell and are used to cause cellular death is briefly described. The steroidal estrogen bearing the boron-cage fragment, when applied in vivo or in vitro, enters the cell which contains an estrophilic receptor, and interacts with the receptor. The steroid-receptor complex is then translated and bound to the nuclear DNA of that cell. Upon irradiation with low energy thermal neutrons, the $^{10}_5B$ nuclei of the dicarbadodecaboranyl substituent capture a neutron and emit a 2.33 MeV alpha particle. The released alpha particle then travels a very short distance and destroys the cellular DNA, thus bringing about the death of the cell.

Because cancerous tissues in the breast, endometrium, and the like, bear high concentrations of estrogen receptors, the use of estratriene or estratetraene compositions containing a dicarbadodecaboranyl substituent at the 17-position, when bound in the nucleus of estrogen sensitive cancers and irradiated with thermal neutrons, effectively and selectively destroys the cancerous tissues. That is, the alpha particles produced by the decay of the boron nucleus in a complex formed by the binding of the dicarbadodecaboranyl estratriene or estratraene and the cytosol estrogen receptor interact directly with nuclear DNA, resulting in the selective destruction of malignant tissues.

The estratriene or estratetraene composition bearing a 17-dicarbadodecaboranyl substituent are used to destroy cancerous cells, in vitro, by adding the composition (from about $10^{-5}$M to about $10^{-9}$M in water) to an estrogen-dependent cancerous cell culture (in concentrations from about 100 to about 1000 cells/ml) such as ZR-75-1 or MCF-7. The concentration of the estratriene or estratetraene composition bearing the 17-dicarbadodecaboranyl substituent must be sufficiently high in order to obtain a concentration of $^{10}_5B$ which ranges from about 15 micrograms per gram of cell to about 300 micrograms per gram of cell. The culture containing the estratriene or estratetraene compositions bearing the 17-dicarbadodecaboranyl substituent are then irradiated with low energy thermal neutrons of about $10^{10}$-$10^{12}$ fluence (1 fluence equals 1 neutron $cm^{-2}sec^{-1}$) for such a time as is necessary to bring about a destruction of the cancerous cell as indicated by the TRYPAN BLUE endpoint.

A significant advantage of the present method is that it utilizes low-energy thermal neutrons, and relatively little normal tissue is damaged. A further advantage of the present method is that the compounds of the present invention possess high estrophilic and uterotropic activity.

EXAMPLE I $(17\beta)$-17-(1,2-dicarbadodecaboran(12)-1-yl)estra-1,3,5(10)-triene-3,17-diol diacetate(II) and 17-(1,2-dicarbadodecaboran(12)-1-yl)estra-1,3,5(10),16-tetraen-3-ol acetate(VIII) are prepared as follows. $(17\alpha)$-19-norpregna-1,3,5(10)-trien-20-yne-3,17-diol diacetate(I) (1.8 g), 40 ml of dried benzene, 40 ml of acetonitrile and 0.85 gms of decaborane are refluxed for 72 hours under a nitrogen atmosphere and the reaction is monitored by thin-layer chromatography (TLC). At the beginning of the reaction, some gas is evolved. After refluxing for 24 hours a number of colored substances, less polar than the starting material, appear in the thin-layer chromatograms.

After refluxing for about 72 hours, the mixture is cooled to room temperature, 20-30 ml of methanol added, and the solution evaporated to dryness under vacuum. Methanol is again added and evaporated. TLC of the Crude reaction mixture indicates that nearly all of (I) reacts and at least 5 compounds are formed, including $(17\beta)$-17-(1,2-dicarbadodecaboran(12)-1-yl)estra-1,3,5(10)-triene-3,17-diol diacetate(II) and 17-(1,2-dicarbadodecaboran(12)-1-yl)estra-1,3,5(10),16-tetraen-3-ol acetate(VIII).

The non-polar reaction products, including the steroid carboranes, are separated from the polar reaction products by dry column chromatography as follows. The dried reaction mixture is dissolved in a minimum amount of methylene chloride and added to silica gel (about 1 to about 2 g), the methylene chloride allowed to evaporate, and the dried silica gel sample added to the top of a 1.5" by 30" nylon tube containing silica gel. The products are eluted with 95% benzene/5% ethyl ether. Polar non-steroidal as well as polar steroidal materials remain on the column.

After evaporation of the eluent solvent, the individual components of the reaction mixture are separated by high pressure liquid chromatography. The mixture of solids (540 mg.) is dissolved in 1.5 ml of methylene chloride containing 25% isooctane and injected onto a silica gel HPLC column. The first fraction (methylene chloride/isooctane) is eluted (A), followed by 1.5 ml of pure methylene chloride (B), and 1.5 ml of 10% methanol in methylene chloride (C). Fractions (A) & (B) are combined, evaporated, redissolved in about 1-2 ml of 75% methylene chloride/25% isooctane, and injected onto an 8 ft silica gel HPLC column. The solvent system is 70% methylene chloride/30% isooctane. Five fractions are collected: (1) 8.9 mg; (2) 49.1 mg; (3) 136.9 mg; (4) 22.2 mg; (5) 207.9 mg. Fraction (5) contains compound (II), which melts at 223°-5° C. Fraction (3) contains compound (VIII), which melts at 182°-5° C. Compound (II) has been fully characterized by IR, UV, mass spectroscopy, elemental analysis, $^1$H-nmr, $^{13}$C-nmr, $^{11}$B-nmr and X-ray crystallography. Compound (VIII) contains one acetyloxy group as indicated by proton nmr and mass spectroscopy. Calculated for $C_{22}H_{34}O_2B_{10}$ 438.622. Calculated for $C_{22}H_{34}O_2B_{10}$·$CH_3CH_2OH$ (484.691, crystallized from ethanol), C 59.47, H 8.32, B 22.31. Found: C 59.87, H 8.44, B 22.40. Mass spectrum: M+439, 440, 441, 442, 398 (394-401), 282, 254, 288. Compound (II) is crystallized from methylene chloride/isoocatane. Calculated for $C_{24}H_{38}O_4B_{10}$ (498.674), C 57.81, H 7.68, B 21.68. Found: C 57.59, H 7.68, B 21.42.

EXAMPLE II $(17\beta)$-17-(1,2-dicarbadodecaboran(12)-1-yl)estra-1,3,5(10)-triene-3,17-diol(IV) is prepared by reaction of $(17\beta)$-17-(1,2-dicarbadodecaboran(12)-1-yl)estra-1,3,5(10)-triene-3,17-diol diacetate(II) with 2 equivalents of 1.0N KOH at 25° C. in methanol for about 1 hour. The reaction products are separated by dry chromatography and HPLC as described in Example I.

EXAMPLE III $(17\beta)$-17-(1,2-dicarbadodecaboran(12)-1-yl)-3-methoxyestra-1,3,5(10)-trien-17-ol acetate(VI) and 1-(3-methoxyestra-1,3,5(10),16-tetraen-17-yl)-1,2-dicarbadodecaborane(12)(VII) are prepared as follows. $(17\alpha)$-3-methoxy-19-norpregna-1,3,5(10)-trien-20-yn-17-ol acetate(V) (5.0 g), 120 ml benzene, 120 ml acetonitrile and decaborane (2.5 g), are combined and refluxed under a nitrogen atmosphere. The reaction is monitored by TLC. The crude reaction mixture contains three principal components as indicated by TLC: $R_f$ 0.47, unreacted (V); $R_f$ 0.61 Compound (VI) (Infrared spectrum: no OH absorption, C-H 3080, 2940; B-H 2580; C=O 1740; 1610, 1500, 1460, 1365; 1250; 1220; 1030); and, $R_f$ 0.72, Compound (VII); (Infrared Spectrum: no OH absorption, C-H 3070, 2930; B-H 2570; no C=O; 1605, 1570, 1560, 1490, 1450, 1275, 1250, 1230, 1150, 1030). (VI) and (VII) are separated and purified by dry column chromatography, followed by HPLC as discussed above in Example I.

EXAMPLE IV $(17\beta)$-17-(1,2-dicarbadodecaboran(12)-1-yl)estra-1,3,5(10)-triene-3,17-diol 17-acetate(III) is prepared by mild base hydrolysis of $(17\beta)$-17-(1,2-dicarbadodecaboran(12)-1-yl)estra-1,3,5(10)-triene-3,17-diol diacetate(II). Into a flask containing 200 mg of (II) are added 20 ml methanol and 1.5 ml 2% (aq.) $KHCO_3$. The solution is stirred overnight, neutralized with 0.1N HCl, evaporated and chromatographed on a preparative TLC plate with 90% methylene chloride/10% ethyl acetate. The area with $R_f$ 0.7 is isolated, crystallized from methanol, and weighs 170 mg. Calculated for $C_{22}H_{36}O_3B_{10}$: C 57.87, H 7.95, B 23.68. Found B 23.56. IR: ($cm^{-1}$) KBr: Broad OH 3400, C-H 3080, 2940, 2860; B-H 2570; C=O 1740; 1620; 1495; 1360, 1220.

EXAMPLE V

Uterotropic Assay (infantile female white swiss mouse), of $(17\beta)$-17-(1,2-dicarbadodecaboran(12)-1-yl)estra-1,3,5(10)-triene-3,17-diol 17-acetate(III) compared to estrone as standard, using 3×3 assay, 5-6 animals per dose indicates that (III) had about 80% of the activity of Estrone. When repeated in a 4×4 assay, 9-10 animals per dose, compound (III) demonstrates a 63% response compared to estrone.

EXAMPLE VI

The Estrogen Receptor assay of compound (III) is performed as follows. Compound (III) competes with 6,7-$^3$H$_2$-estradiol for the binding site of the Calf uterine cytosolic estrogen receptor. This compound exhibits a 50% inhibition to binding at 1 Mole equivalent, whereas diethylstilbestrol requires somewhat greater than 10 Mole equivalents to accomplish 50% inhibition to binding. These assays serve to demonstrate that (III) is at least two orders of magnitude greater in estrophilic activity than "estradiol-17β 3-caboranylmethyl ether" discussed in Steroids 37, 223 (1981).

I claim:

1. A member selected from the group consisting of an estratriene composition of the formula:

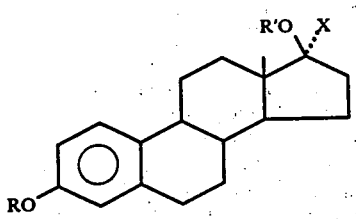

and an estratetraene composition of the formula:

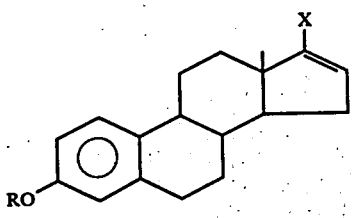

wherein R, and R' are independently selected from the group consisting of hydrogen, acetyl, and methyl groups, and wherein X is a dicarbadodecaboranyl substituent of the formula C$_2$B$_{10}$H$_{11}$.

2. An estrogen composition selected from the group consisting of:
   (17β)-17-(1,2-Dicarbadodecaboran(12)-1-yl)estra-1,3,5(10)-triene, 3,17-diol diacetate
   (17β)-17-(1,2-Dicarbadodecaboran(12)-1-yl)estra-1,3,5(10)-triene-3,17-diol 17-acetate
   (17β)-17-(1,2-Dicarbadodecaobran(12)-1-yl)estra-1,3,5(10)-triene-3,17-diol
   (17β)-17-(1,2-Dicarbadodecaboran(12)-1-yl)-3-methoxyestra-1,3,5(10)-trien-17-ol acetate
   1-(3-Methoxyestra, 1,3,5(10),16-tetraen-17-yl)-1,2-dicarbadodecaborane(12)
   17-(1,2-Dicarbadodecaboran(12)-1-yl)estra-1,3,5(10),16-tetraen-3-ol acetate.

3. A method of preparation of estrogen compositions having a dicarbadodecaboranyl substituent at the 17-position comprising the steps of:
   reacting an estratriene composition of the formula:

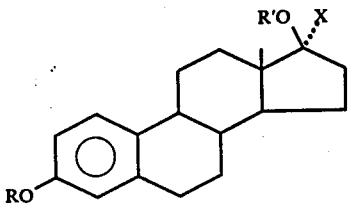

wherein X is an acetylenic substituent; and wherein R and R' are independently selected from the group comprising hydrogen, acetyl, and methyl; with decaborane in a refluxing, dry organic solvent, for such a time as is necessary to effect condensation; and, separating the reaction products.

4. A method, as claimed in claim 3, wherein said estrogen composition is selected from the group consisting of:
   (17β)-17-(1,2-Dicarbadodecaboran(12)-1-yl)estra-1,3,5(10)-triene-3,17-diol diacetate
   (17β)-17-(1,2-Dicarbadodecaboran(12)-1-yl)-3-methoxyestra-1,3,5(10)-trien-17-ol acetate
   1-(3-Methoxyestra- 1,3,5(10),16-tetraen-17-yl)-1,2-dicarbadodecaborane(12)
   17-(1,2-Dicarbadodecaboran(12)-1-yl)estra-1,3,5(10),16-tetraen-3-ol acetate.

5. A method of preparation of (17β)-17-(1,2-dicarbadodecaboran(12)-1yl)estra-1,3,5(10)-triene-3,17-diol or (17β)-17-(1,2-dicarbadodecaboran(12)-1-yl)estra-1,3,5(10)-triene-3,17-diol 17-acetate comprising the step of:
   reacting (17β)-17-(1,2-dicarbadodecaboran(12)-1-yl)estra-1,3,5(10)-triene-3,17-diol diacetate with base for such a time as necessary to bring about hydrolysis.

6. A method for the destruction of cancerous tissues containing estrogen receptors comprising the steps of:
   administering an effective dose of an estratriene or estratetraene composition bearing a dicarbadodecaboranyl substituent at the 17-position;
   irradiating the area of the cancerous tissue with low energy thermal neutrons of about $10^{10}$ to about $10^{12}$ fluence for such a time as is necessary to bring about destruction of the cancerous cells.

7. A method, as claimed in claim 6, wherein said estratriene or estratetraene composition is selected from the group consisting of:
   (17β)-17-(1,2-Dicarbadodecaboran(12)-1-yl)estra-1,3,5(10)-triene-3,17-diol diacetate
   (17β)-17-(1,2-Dicarbadodecaboran(12)-1-yl)estra-1,3,5(10)-triene-3,17-diol 17-acetate
   (17β)-17-(1,2-Dicarbadodecaboran(12)-1-yl)estra-1,3,5(10)-triene-3,17-diol
   (17β)-17-(1,2-Dicarbadodecaboran(12)-1-yl)-3-methoxyestra-1,3,5(10)-trien-17-ol acetate
   1-(3-Methoxyestra-1,3,5(10),16-tetraen-17-yl)-1,2-dicarbadodecaborane(12)
   17-(1,2-Dicarbadodecaboran(12)-1-yl)estra-1,3,5(10),16-tetraen-3-ol acetate.

8. A method as claimed in claim 7, wherein the effective dose is a $^{10}_5$B concentration of at least about 15 micrograms per gram of cell, but less than about 300 micrograms per gram of cell.

* * * * *

UNITED STATES PATENT AND TRADEMARK OFFICE
CERTIFICATE OF CORRECTION

PATENT NO. : 4,466,952

DATED : August 21, 1984

INVENTOR(S) : Harry E. Hadd

It is certified that error appears in the above—identified patent and that said Letters Patent is hereby corrected as shown below:

On the title page:
In References Cited, Column 2, line 8, "Estradiol-178" should read --Estradiol-17β--.

Column, 3, line 34, insert "dicarbadodecaboranyl" in Column 17a.

Column 3, line 64, "benzeneacetonitrile" should read --benzene-acetonitrile--.

Column 4, line 2, "-3,17-diol" (second occurrence) should be omitted.

Column 4, line 17, "3," should be omitted.

Column 4, lines 53-54, "estratraene" should be --estratetraene--.

Column 7, line 52, "Dicarbadodecaobran" should read --Dicarbadodecaboran--.

Column 7, line 57, "1-(3-Methoxyestra, 1" should read --1-(3-Methoxyestra-1--.

UNITED STATES PATENT AND TRADEMARK OFFICE
CERTIFICATE OF CORRECTION

PATENT NO. : 4,466,952                Page 2 of 2

DATED      : August 21, 1984

INVENTOR(S) : Harry E. Hadd

It is certified that error appears in the above-identified patent and that said Letters Patent is hereby corrected as shown below:

Column 1, " 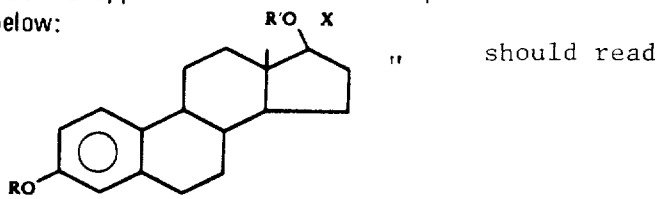 " should read

-- 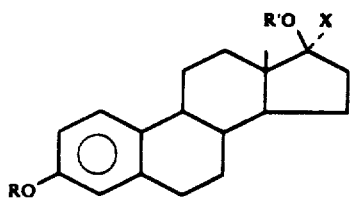 --

Column 2, " 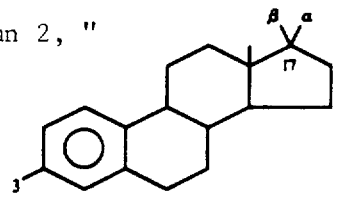 " should read -- 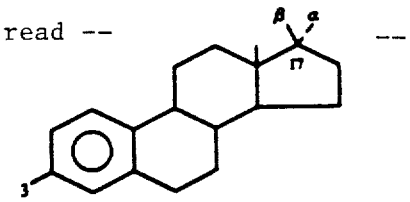 --

𝕾igned and 𝕾ealed this

Sixteenth Day of April 1985

[SEAL]

Attest:

DONALD J. QUIGG

Attesting Officer    Acting Commissioner of Patents and Trademarks